(12) United States Patent
Wang et al.

(10) Patent No.: US 10,345,304 B2
(45) Date of Patent: Jul. 9, 2019

(54) MULTIFUNCTIONAL NANOPROBE-ENABLED CAPTURE AND EARLY DETECTION OF MICROBIAL PATHOGENS

(71) Applicant: THE JOHNS HOPKINS UNIVERSITY, Baltimore, MD (US)

(72) Inventors: Chao Wang, Fairfax, VA (US); Kellogg Schwab, Baltimore, MD (US); Charles Young, Mount Airy, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/950,367

(22) Filed: Nov. 24, 2015

(65) Prior Publication Data

US 2016/0146813 A1 May 26, 2016

Related U.S. Application Data

(60) Provisional application No. 62/084,361, filed on Nov. 25, 2014.

(51) Int. Cl.
| | | |
|---|---|---|
| *G01N 33/569* | (2006.01) | |
| *G01N 33/543* | (2006.01) | |
| *G01N 21/552* | (2014.01) | |
| *G01N 21/64* | (2006.01) | |

(52) U.S. Cl.
CPC ..... *G01N 33/56983* (2013.01); *G01N 21/554* (2013.01); *G01N 21/648* (2013.01); *G01N 33/54326* (2013.01); *G01N 33/54366* (2013.01); *G01N 33/56916* (2013.01); *G01N 2201/062* (2013.01); *G01N 2333/08* (2013.01); *G01N 2333/245* (2013.01)

(58) Field of Classification Search
CPC ............. G01N 21/6486; G01N 33/569; G01N 33/56911; G01N 2035/00326; G01N 35/00; G01N 35/00871; G01N 35/0092; G01N 1/38; C12Q 1/6883; C12Q 1/70; B82Y 10/00; B82Y 20/00; B82Y 5/00; B01L 7/52; B01L 2200/04; B01J 19/0046; B01J 2219/00283; B01J 2219/00292; B01J 2219/00315; A61B 5/150755; A61B 5/15; A61B 5/151
See application file for complete search history.

(56) References Cited

U.S. PATENT DOCUMENTS

2014/0170669 A1* 6/2014 Vandervest ...... G01N 33/54366
435/6.15

OTHER PUBLICATIONS

Swanson et al. (Sensors Jul. 2009, 9, 5783-5809).*
Liu et al. Nano Lett, 2013 13, 4333-4339.*
Levin et al. ACS Nano vol. 3 No. 6 1379-1388 2009.*
Peng et al. (Agnew Chem Int. Ed. 2011, 50, 3158-3163 (Year: 2011).*
Xu et al., "Au—Fe3O4 Dumbbell Nanoparticles as Dual-Functional Probes," Angew. Chem. Int. Ed, 2008, 47, 173-176.

* cited by examiner

*Primary Examiner* — Sally A Merkling
(74) *Attorney, Agent, or Firm* — Casimir Jones, S.C.; Jeffrey W. Childers

(57) ABSTRACT

The presently disclosed fluidic sensor system and method comprise multifunctional nanoprobe-enabled capture for early detection of chemical and/or biological pathogens in a liquid sample. This sensor system and method can be used for food and environmental monitoring.

16 Claims, 3 Drawing Sheets

MULTIFUNCTIONAL NANOPROBE-ENABLED CAPTURE AND EARLY DETECTION OF MICROBIAL PATHOGENS

CROSS-REFERENCE TO RELATED APPLICATIONS

This application claims the benefit of U.S. Provisional Application No. 62/084,361, filed Nov. 25, 2014, which is incorporated herein by reference in its entirety.

BACKGROUND

Conventional food and environmental monitoring relies on laboratory-based biochemical methods, such as polymerase chain reaction (PCR) and enzyme-based immunosorbent assays (ELISA). While these methods are well-established and possess high sensitivity and specificity, they are usually time-consuming (a few days, including sample transportation and analysis), involve laborious processes, and need skilled personnel to perform the analysis. Moreover, such processes usually require sophisticated facilities and strict cleaning standards, prohibiting operation in adverse field conditions. Owing to these challenges, chemical and biological sensors that integrate elements for chemical and biological recognition, respectively, and signal transduction have emerged as robust and state-of-the-art detection techniques for food- and water-borne pathogens.

In sensors, chemical or microbial pathogens are usually recognized by target specific interactions, such as antibody-antigen binding and DNA hybridization, which are then identified by electrochemically, optically, piezoelectrically, or thermally sensitive devices. Enabled by the recent advances in nanomaterials and nanotechnologies, miniaturization of sensing devices has achieved lab-on-a-chip designs that enable portable, cost-effective biosensors that are capable of near real-time (in a few minutes) detection under field conditions. Despite the progress that has been made, a universal challenge for existing sensing technologies is their relatively low sensitivity (e.g., >10 colony-forming units (cfu)/mL) compared to laboratory-based chemical and biochemical methods. Such relatively low sensitivity is primarily due to the reduced device sizes that have limited the number of targets for recognition. This challenge has placed substantial problems on using sensors for detection of pathogens at ultralow concentrations (i.e., <10 cfu/mL).

To approach or achieve high sensitivity, current sensors usually require an additional enrichment stage prior to detection, which can extend the processing time by hours. In contrast, molecularly functionalized magnetic nanoparticles are able to capture pathogenic chemicals or organisms by magnet in batch processes, with demonstrated detection at concentrations as low as approximately 4 cfu/mL. Moreover, magnetic beads have been widely used as labels for genetic detection by using magnetometers, such as superconducting quantum interference device (SQUID), magnetoresitive sensors, and diagnostic magnetic resonance assays. The weak magnetic dipole interactions, however, have limited the sensitivity (e.g., up to approximately 100 cfu for a stream of 10 μL sample) of magnetic sensors. Meanwhile, the commercially viable magnetic probes usually comprise particles of micrometer-scale sizes. Such large probes have limited the number of particles of uptake per pathogen, leading to poor specificity and detection limits.

SUMMARY

In some aspects, the presently disclosed subject matter provides a sensor system for detecting at least one chemical and/or biological pathogen in a liquid sample, the sensor system comprising: (a) a nanoprobe comprising a plasmonic nanoparticle and a magnetic particle; (b) a flow cell comprising a channel capable of holding a liquid sample comprising at least one chemical and/or biological pathogen and the nanoprobe; (c) a magnet placed in close proximity to the flow of the liquid sample, wherein the magnet is capable of capturing the nanoprobe when the nanoprobe is bound to the at least one chemical and/or biological pathogen; and (d) an optical transducer comprising a light source and a photodetector, wherein the optical transducer is capable of detecting the nanoprobe bound to the at least one chemical and/or biological pathogen. In some embodiments, the nanoprobe is functionalized with at least one targeting molecule via a linker molecule.

In some aspects, the presently disclosed subject matter provides a sensing technology for detecting chemical or biological pathogens in a sample, the sensor system comprising: (a) a nanoprobe comprising a plasmonic nanoparticle and a magnetic particle and functionalized with at least one targeting molecule via a linker molecule; (b) a flow cell comprising a channel capable of holding a flow of liquid comprising the nanoprobe and the analyte; (c) a magnet placed in close proximity to the flow which is capable of capturing the nanoprobe when the nanoprobe is bound to at least one pathogenic species; and (d) an optical transducer comprising a light source and a photodetector, wherein the optical transducer is capable of detecting the nanoprobe bound to at least one pathogen.

In some embodiments, at least one targeting molecule is selected from the group consisting of an antibody, an enzyme, a peptide, a protein, a nucleic acid, and an oligonucleotide. In some embodiments, at least one targeting molecule is an antibody. In some embodiments, the antibody is an immunoglobulin G (IgG) antibody.

In some embodiments, the photodetector comprises a microscope or a spectrometer. In some embodiments, the magnet is optimized to capture the nanoprobe when it is bound to the at least one chemical and/or biological pathogen and not capture the nanoprobe when it is not bound to the at least one chemical and/or biological pathogen. In some embodiments, the magnet is a solenoid. In some embodiments, the light source is a light emitting diode (LED). In some embodiments, the plasmonic nanoparticle comprises gold, silver, nickel, copper, titanium, silicon, galadium, palladium, platinum, and/or chromium. In some embodiments, the magnetic particle comprises iron, nickel, and/or cobalt.

In some embodiments, the linker molecule comprises a polyether linkage. In some embodiments, the linker molecule comprises a HS-polyethylene glycol-COOH linkage or a dopamine-polyethylene glycol-COOH linkage.

In some embodiments, at least one biological pathogen is selected from the group consisting of a bacterium, protozoan, protist, fungus, parasite, and a virus. In some embodiments, at least one chemical and/or biological pathogen is *Escherichia coli* (*E. coli*) or a norovirus. In some embodiments, the liquid sample comprises filtered food and/or water.

In some aspects, the presently disclosed subject matter provides a method for determining the presence of at least one chemical and/or biological pathogen in a liquid sample, the method comprising: (a) providing a sensor system comprising: (i) at least one nanoprobe comprising a plasmonic nanoparticle and a magnetic particle; (ii) a flow cell comprising a channel capable of holding a liquid sample comprising at least one chemical and/or biological pathogen and the at least one nanoprobe; (iii) a magnet placed in close proximity to the flow of the liquid sample, wherein the magnet is capable of capturing the at least one nanoprobe when the at least one nanoprobe is bound to the at least one chemical and/or biological pathogen; and (iv) an optical transducer comprising a light source and a photodetector, wherein the optical transducer is capable of detecting the at least one nanoprobe bound to the at least one chemical and/or biological pathogen; (b) contacting a liquid sample comprising at least one chemical and/or biological pathogen with the at least one nanoprobe comprising a plasmonic nanoparticle and a magnetic particle to form at least one nanoprobe conjugated with at least one chemical and/or biological pathogen; (c) adding the liquid sample comprising the at least one nanoprobe conjugated with at least one chemical and/or biological pathogen to the channel of the flow cell; (d) capturing the at least one nanoprobe conjugated with at least one chemical and/or biological pathogen using the magnet; and (e) detecting the presence of the at least one nanoprobe conjugated with at least one chemical and/or biological pathogen using the optical transducer, thereby detecting the presence of at least one chemical and/or biological pathogen in the liquid sample. In some embodiments, the nanoprobe is functionalized with at least one targeting molecule via a linker molecule.

In some aspects, the presently disclosed subject matter provides a method for determining the existence or absence of a chemical or biological pathogen in a sample, the method comprising: (a) obtaining the sample; (b) adding to the sample at least one nanoprobe comprising a plasmonic nanoparticle and a magnetic particle and functionalized with at least one targeting molecule via a linker molecule; (c) allowing at least one nanoprobe to react with at least one pathogen if present in the sample to form at least one nanoprobe conjugated with a pathogen; (d) adding the sample to the channel of the sensor system disclosed herein; (e) capturing the at least one nanoprobe conjugated with a pathogen if present by the magnet of the system; and (f) detecting the presence or absence of the at least one nanoprobe conjugated with a pathogen.

In some embodiments, the method can detect the at least one chemical and/or biological pathogen at a concentration of about 10 cfu/mL or lower. In some embodiments, at least one targeting molecule is selected from the group consisting of an antibody, an enzyme, a peptide, a protein, a nucleic acid, and an oligonucleotide. In some embodiments, at least one targeting molecule is an antibody. In some embodiments, at least one targeting molecule is an immunoglobulin G (IgG) antibody.

In some embodiments, at least one biological pathogen is selected from the group consisting of a bacterium, protozoan, protist, fungus, parasite, and a virus. In some embodiments, at least one chemical and/or biological pathogen is *Escherichia coli* (*E. coli*) or a norovirus.

In some embodiments, the magnet is a solenoid. In some embodiments, the photodetector comprises a microscope or a spectrometer. In some embodiments, the light source is a light emitting diode (LED).

In some embodiments, the plasmonic nanoparticle comprises gold, silver, nickel, copper, titanium, silicon, galadium, palladium, platinum, and/or chromium. In some embodiments, the magnetic particle comprises iron, nickel, and/or cobalt.

In some embodiments, the linker molecule comprises a polyether linkage. In some embodiments, the linker molecule comprises a HS-polyethylene glycol-COOH linkage or a dopamine-polyethylene glycol-COOH linkage.

In some embodiments, determining the presence of at least chemical and/or biological pathogen occurs in realtime. In some embodiments, adding the liquid sample comprising at least one nanoprobe conjugated with at least one chemical and/or biological pathogen to the channel of the sensor system occurs before or concurrently with contacting the liquid sample comprising at least one chemical and/or biological pathogen to at least one nanoprobe comprising a plasmonic nanoparticle and a magnetic particle to form at least one nanoprobe conjugated with at least one chemical and/or biological pathogen. In some embodiments, the liquid sample comprises filtered food and/or water.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
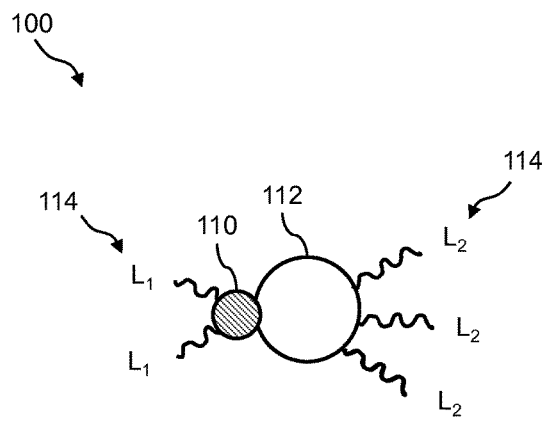
Figure 1B:
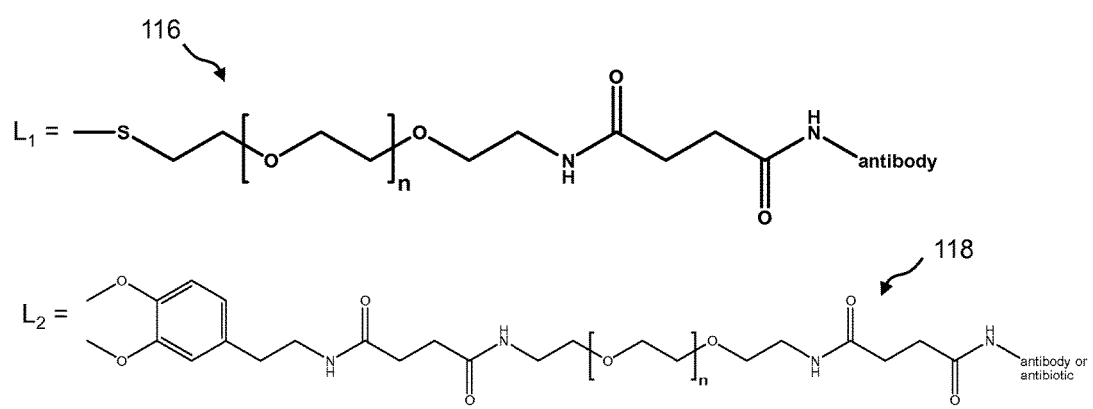
Figure 2:
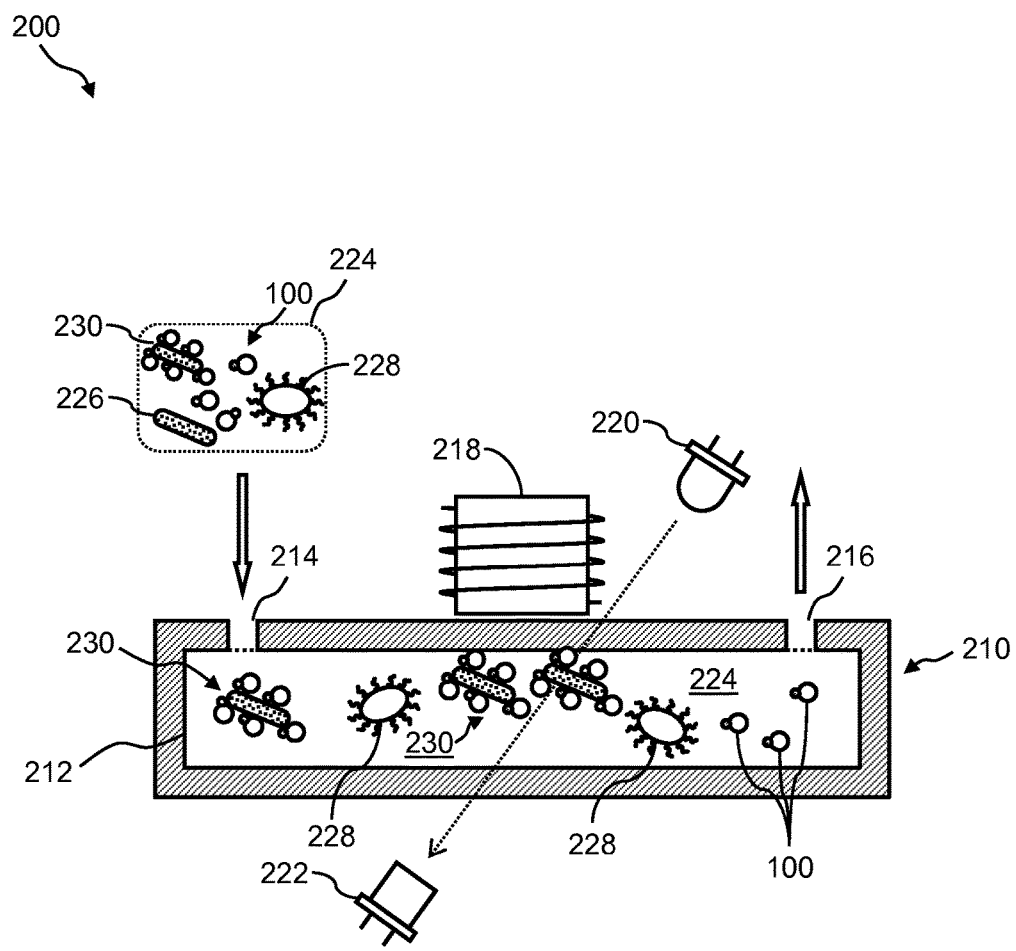
Figure 3:
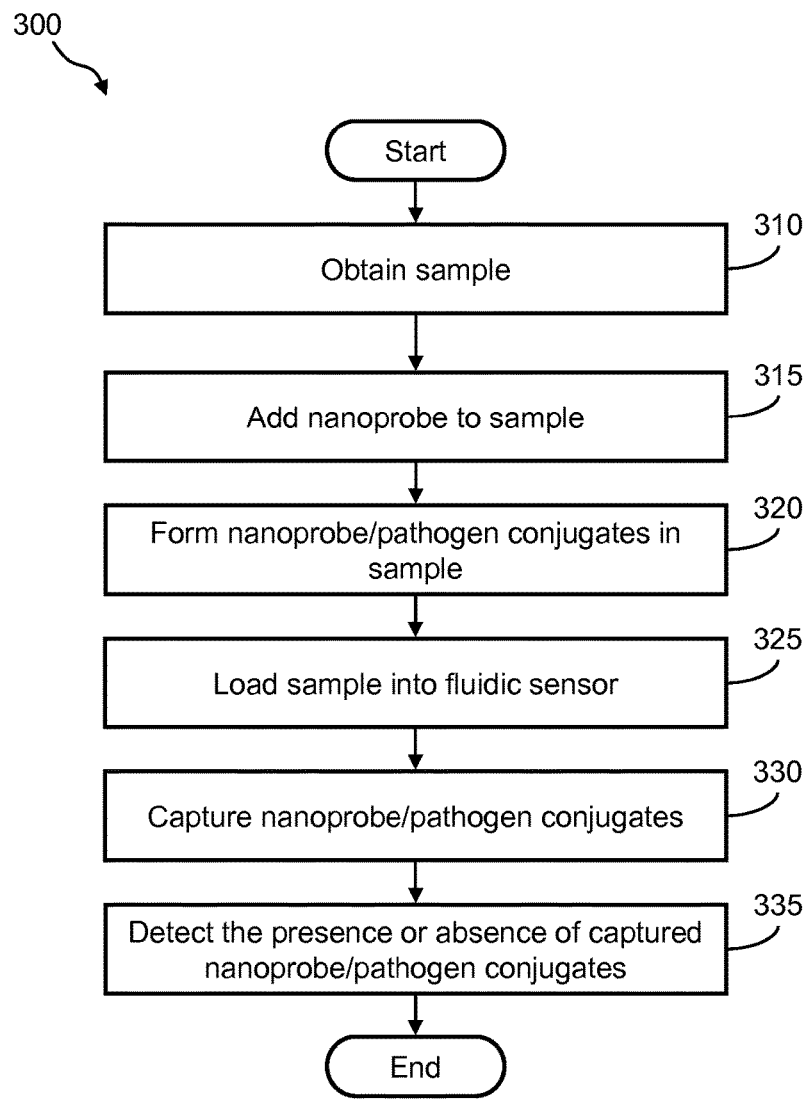

Having thus described the presently disclosed subject matter in general terms, reference will now be made to the accompanying Figures, which are not necessarily drawn to scale, and wherein:

FIG. 1A and FIG. 1B show a schematic diagram of an example of a multifunctional nanoprobe (FIG. 1A) and the structural formulas of examples of a first linker molecule and a second linker molecule (FIG. 1B) that are used to anchor sensing molecules to form the multifunctional nanoprobe of FIG. 1A;

FIG. 2 shows a side view of an example of a fluidic sensor system and illustrates a representative process for the capture and early detection of a pathogen using the multifunctional nanoprobe of FIG. 1A; and FIG. 3 shows a flow diagram of an example of a method of using a multifunctional nanoparticle and fluidic sensor system for determining the existence or absence of a pathogen in a sample.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides a sensor device and sensing method for early detection of chemical and microbial pathogens. As used herein, the term "early detection" of a pathogen refers to the detection of a pathogen when the pathogen is still found in low concentrations. In some embodiments, the presently disclosed methods can detect a pathogen at a concentration of about 10 cfu/mL or lower. In some embodiments, the optical transducers used in the presently disclosed device are much more sensitive than magnetic detectors known in the art and have great potential for device miniaturization, cost reduction, simplified operation, and field applications. In some embodiments, the presently disclosed subject matter combines the advantages of magnetic capture and optical transduction and is capable of rapid, sensitive, and specific detection of pathogens in portable devices and field conditions.

More particularly, in some embodiments, the presently disclosed subject matter discloses a multifunctional nanoprobe comprising a plasmonic-magnetic heterodimer nanoparticle. In some embodiments, the multifunctional nanoprobe is functionalized with targeting molecules. This multifunctional nanoprobe can be used to recognize and label chemical and microbial pathogens in a flowing stream carrying analytes, for example. To achieve an ultralow detection limit (<10 cfu/mL), a magnet, such as a solenoid, is used to capture the pathogen/nanoparticle conjugates in the flow. Once the conjugates are captured, they can be analyzed by an optical transducer. In some embodiments, untargeted microorganisms and other species, as well as non-specific binding nanoparticles, will not respond to the magnetic capturing and will be washed away by the stream.

I. Multifunctional Nanoprobe for Capture and Early Detection of Pathogens

In some embodiments, the presently disclosed subject matter provides a multifunctional nanoprobe for capture and early detection of a chemical and/or biological pathogen. In some embodiments, a sensor system is disclosed for detecting at least one chemical and/or biological pathogen in a liquid sample, the sensor system comprising: (a) a nanoprobe comprising a plasmonic nanoparticle and a magnetic particle; (b) a flow cell comprising a channel capable of holding a liquid sample comprising at least one chemical and/or biological pathogen and the nanoprobe; (c) a magnet placed in close proximity to the flow of the liquid sample, wherein the magnet is capable of capturing the nanoprobe when the nanoprobe is bound to the at least one chemical and/or biological pathogen; and (d) an optical transducer comprising a light source and a photodetector, wherein the optical transducer is capable of detecting the nanoprobe bound to the at least one chemical and/or biological pathogen.

For example, FIG. 1A shows a schematic diagram of an example of a multifunctional nanoprobe 100. Multifunctional nanoprobe 100 is a heterodimer nanoparticle comprising a plasmonic nanoparticle 110 and a magnetic nanoparticle 112. In one example, plasmonic nanoparticle 110 is a gold (Au) nanoparticle and magnetic nanoparticle 112 is an iron oxide ($Fe_3O_4$) nanoparticle.

As used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 10 nm. In some embodiments, the nanoparticle has a diameter of about 100 nm. In other embodiments, the nanoparticle has a diameter of about 500 nm. In yet other embodiments, the nanoparticle has a diameter of about 1000 nm (1 µm).

In this example, plasmonic nanoparticle 110 and magnetic nanoparticle 112 have a spherical shape, but it will be appreciated by one of ordinary skill in the art that nanoparticles suitable for use with the presently disclosed methods can exist in a variety of shapes, including, but not limited to, spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes.

Multifunctional nanoprobe 100 is a plasmonic-magnetic nanoparticle. As used herein, a "plasmonic-magnetic nanoparticle" is a nanoparticle with both plasmonic and magnetic characteristics. Plasmonic nanoparticles are particles whose electron density can couple with electromagnetic radiation of wavelengths that are far larger than the particle due to the nature of the dielectric-metal interface between the medium and the particles. This characteristic is in contrast to a pure metal where there is a maximum limit on what size wavelength can be effectively coupled based on the material size. Plasmonic nanoparticles are different from normal surface plasmons because they also exhibit scattering, absorbance, and coupling properties based on their geometries and relative positions. Plasmons are the oscillations of free electrons that are the consequence of the formation of a dipole in the material due to electromagnetic waves. The electrons migrate in the material to restore its initial state; however, the light waves oscillate, leading to a constant shift in the dipole that forces the electrons to oscillate at the same frequency as the light. This coupling only occurs when the frequency of the light is equal to or less than the plasma frequency and is greatest at the plasma frequency that is therefore called the resonant frequency. The scattering and absorbance cross-sections describe the intensity of a given frequency to be scattered or absorbed.

In some embodiments, the plasmonic nanoparticle comprises a metal, metallic composite, metal oxide, metallic salt, electric conductor, electric superconductor, electric semiconductor, dielectric, quantum dot or composite from a combination thereof. In some embodiments, the plasmonic particles comprise any geometric shape currently known or to be created that absorb light and generate plasmon resonance at a desired wavelength, including nanoplates, solid nanoshells, hollow nanoshells, nanorods, nanorice, nanospheres, nanofibers, nanowires, nanopyramids, nanoprisms, nanostars or a combination thereof. In some embodiments, the plasmonic particles comprise silver, gold, nickel, copper, titanium, silicon, galadium, palladium, platinum, or chromium. Plasmonic nanoparticles commonly comprise metal materials, particularly noble metals (e.g. silver (Ag) and gold (Au)). In some embodiments, the plasmonic nanoparticle comprises gold (Au). In some embodiments, the plasmonic nanoparticle comprises silver (Ag). In some embodiments, the plasmonic nanoparticle comprises gold (Au) and/or silver (Ag). In some embodiments, the plasmonic nanoparticle comprises copper (Cu). In some embodiments, the plasmonic nanoparticle comprises gold (Au) and/or copper (Cu). In some embodiments, the plasmon resonance generates optical signals in the wavelength range of about 100 to about 1000 nm.

Magnetic nanoparticles can be manipulated using a magnetic field. Such magnetic particles commonly comprise magnetic elements, such as iron, nickel and cobalt, and their chemical compounds. In some embodiments, alloys of these metals with each other and with other elements can also be manipulated using a magnetic field. In some embodiments, the magnetic particle comprises iron, nickel, and/or cobalt. In some embodiments, the magnetic particle comprises iron. In some embodiments, the magnetic particle comprises only iron and no other chemical element. In some embodiments, the magnetic particle comprises nickel. In some embodiments, the magnetic particle comprises only nickel and no other chemical element. In some embodiments, the magnetic particle comprises cobalt. In some embodiments, the magnetic particle comprises only cobalt and no other chemical element. In some embodiments, the magnetic particle comprises iron oxide ($Fe_3O_4$).

Multifunctional nanoprobe 100 is functionalized with targeting molecules 114. Targeting molecules 114 are anchored to plasmonic nanoparticle 110 and magnetic particle 112 via linker molecules to form multifunctional nanoprobe 100. FIG. 1B shows the structural formulas of examples of a first linker molecule 116 and a second linker molecule 118 that are used to anchor targeting molecules 114 to form multifunctional nanoprobe 100. In one example, targeting molecules 114 are microbial specific IgG antibodies.

Accordingly, in some embodiments, the nanoprobe is functionalized with at least one targeting molecule via a linker molecule. As used herein, the term "targeting molecule" refers to a molecule that can recognize a chemical or biological pathogen using a target-specific interaction. Non-limiting examples of targeting molecules include: (a) natural biomolecules: single or double stranded nucleic acids (DNA or RNA), enzymes, antibodies, membrane proteins, heat shock proteins, chaperonins, other proteins, monosaccharides, polysaccharides, glycoproteins, fatty acids, terpenes, steroids, other molecules of a lipid nature, lipoproteins, hormones, vitamins, metabolites, hydrocarbons, natural molecules with antibiotic or antiviral activity, or macromolecular aggregates formed by proteins and/or nucleic acids or other combinations of the previously mentioned molecules; (b) natural biomolecules obtained by in vitro selection processes: aptamers, ribozymes or aptazymes; (c) artificial biomolecules: analogs of natural nucleic acids, natural and artificial nucleic acid chimers, polymers with the capacity to recognize shapes ("molecular imprinted polymers" or MIPs), artificial antibodies, recombinant antibodies, miniantibodies or synthetic molecules with antibiotic or antiviral activity; (d) natural or artificial chemical agents with functional groups that specifically bind to chemical or biological species: carboxyl, amine, hydroxyl, sulfonate, nitrate, ester, alkane, alkene, alkyne, phenyl, benzyl, halo, carbonyl, aldehyde, imide, azide, nitrile, sulfhydryl, (di)sulfide, sulfo, phosphate; and (e) natural or artificial chelating agents that can selectively bind to chemical or biological species: ethylenediamine, ethylenediaminetetraacetic acid, dimercaprol, ligno sulfonates, humic or fulvic acids, citric acid, and amino acids.

In particular embodiments, the targeting molecules include antibodies, peptides, proteins, enzymes, nucleic acids, and oligonucleotides. In some embodiments, at least one targeting molecule is selected from the group consisting of an antibody, an enzyme, a peptide, a protein, a nucleic acid, and an oligonucleotide. In some embodiments, a nanoprobe is functionalized by more than one type of targeting molecule, such that the nanoprobe can target more than one type of chemical and/or biological pathogen.

The biologically specific interaction when the targeting molecules 114 on multifunctional nanoprobe 100 is bound to a biological pathogen may be noncovalent or covalent. In some embodiments, the biologically specific interaction occurs via bioconjugation or crosslinking As used herein, the term "bioconjugation" refers to the chemical strategy that forms a stable covalent link between two biomolecules. As used herein, the term "crosslinking" refers to the process of linking one polymer chain to another by covalent bonds or ionic bonds.

As used herein, the term "antibody" refers to a polypeptide or group of polypeptides which comprise at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab)$_2$, and F(ab')$_2$ fragments. As used herein, the terms "Immunoglobulin G" and "IgG" refer to an antibody isotype. IgG is a protein complex composed of four peptide chains, two identical heavy chains and two identical light chains, arranged in a Y-shape typical of antibody monomers. Each IgG has two antigen binding sites. In some embodiments, at least one targeting molecule is an antibody. In some embodiments, the antibody is selected from the group consisting of IgG, IgA, IgD, IgE, and IgM. In some embodiments, at least one targeting molecule is an immunoglobulin G (IgG) antibody. In some embodiments, at least one targeting molecule is an immunoglobulin A (IgA) antibody. In some embodiments, at least one targeting molecule is an immunoglobulin D (IgD) antibody. In some embodiments, at least one targeting molecule is an immunoglobulin E (IgE) antibody. In some embodiments, at least one targeting molecule is an immunoglobulin M (IgM) antibody.

In some embodiments, at least one targeting molecule is a peptide. In some embodiments, the peptide is targeted to the nucleus. In some embodiments, the peptide is NLS (-Pro-Pro-Lys-Lys-Lys-Arg-Lys-Val-). In some embodiments, the peptide is targeted to the mitochondrial matrix. In some embodiments, the peptide is $H_2N$-Met-Leu-Ser-Leu-Arg-Gln-Ser-Ile-Arg-Phe-Phe-Lys-Pro-Ala-Thr-Arg-Thr-Leu-Cys-Ser-Ser-Arg-Tyr-Leu-Leu. In some embodiments, the peptide is targeted to the peroxisome. In some embodiments, the peptide is PTS1 or PTS2.

As used herein, the term "protein" refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. As used herein, the term "enzyme" refers to a biological catalyst, such as a protein or a catalytic RNA molecule.

The term "nucleic acid" is used herein interchangeably with "polynucleotide" to indicate a polymer of nucleosides. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However, the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. As used herein, the term "oligonucleotide" is also a polymer of nucleosides, but is generally considered to be a shorter polymer of nucleosides, such as at least 10, 20, 30, 40, 50, 60, 70, 80, 90, 100, 150, 200, 300, or 500 bases in length.

In some embodiments, a linker molecule is conjugated to the nanoprobe, either on the plasmonic nanoparticle, on the magnetic particle, or on both. In some embodiments, the linker molecule can be any molecule that is capable of being conjugated to the nanoprobe and to at least one targeting molecule. In some embodiments, the linker molecule comprises a polyethylene glycol linkage. In some embodiments, the linker molecule comprises a polyethylene glycol (PEG) linkage or a derivative thereof. In some embodiments, the linker molecule comprises a HS-polyethylene glycol-COOH linkage. In some embodiments, the linker molecule comprises a dopamine-polyethylene glycol-COOH linkage. In some embodiments, the linker molecule comprises HS-polyethylene glycol-COOH or dopamine-polyethylene glycol-COOH. In some embodiments, the linker molecule comprises a HS-polyethylene glycol-COOH linkage or a dopamine-polyethylene glycol-COOH linkage.

II. Sensor System for Capture and Early Detection of Pathogens

In some embodiments, the presently disclosed subject matter provides a sensor system for early detection of a pathogen. As used herein, the terms "sensor" and "sensor system" refer to a system combining a probe with a physicochemical detector, which can be used for detecting a substance, such as a chemical or biological pathogen, in a sample.

Referring now to FIG. 2 is a side view of an example of a fluidic sensor system 200 and illustrates a process for the capture and early detection of a pathogen using multifunctional nanoprobes 100 of FIG. 1A. Fluidic sensor system 200 includes a flow cell 210. Flow cell 210 has a channel 212, which has an inlet 214 and an outlet 216. As used herein, the term "channel" refers to a path through which liquid can flow. In some embodiments, the channel ranges in width from about 10 nanometers to about 1 meter. In some embodiments, the channel is larger than 1 meter in width. In some embodiments, the channel ranges in width from about 10 nanometers to about 0.5 meter. In some embodiments, the channel is less than about 0.5 meter, such as less than about 0.1 meter, 0.01 meter, or 0.001 meter.

A magnet 218 (e.g., an electromagnet or permanent magnet) is provided in close proximity to flow cell 210. Namely, magnet 218 is placed so that channel 212 of flow cell 210 is within the magnetic field of magnet 218. As used herein, the term "magnet" refers to an object that is surrounded by a magnetic field and that has the property, either natural or induced, of attracting iron or steel. In one example, magnet 218 is a solenoid. As used herein, the term "solenoid" refers to a current-carrying coil of wire that acts like a magnet when a current is passed through it. In some embodiments, the magnet is optimized to capture the nanoprobe when the nanoprobe is bound to a pathogen, but does not capture the nanoprobe when the nanoprobe is not bound to a pathogen. In some embodiments, the magnet is optimized to capture the nanoprobe when it is bound to at least one pathogen and not capture the nanoprobe when it is not bound to at least one pathogen. In some embodiments, the magnet is a solenoid. The term "optimized" as used in this context refers to adjusting the strength of the magnet to allow free nanoprobes to be carried away by the flow, but allow the nanoprobes bound to a pathogen to be captured.

For optical detection, fluidic sensor system 200 includes an optical transducer comprising a light source 220 (e.g., a light emitting diode (LED)) and a photodetector 222 for detecting the interaction of a pathogen with multifunctional nanoprobe 100. In some embodiments, the light source is a light emitting diode (LED). In some embodiments, the light source is a Xenon arc lamp. In some embodiments, the light source is a tungsten-halogen lamp. In some embodiments, the light source is a laser. In some embodiments, the laser is an argon-ion laser. In some embodiments, the laser is a Krypton-ion laser. In some embodiments, the light source is an electronic flash tube.

As used herein, an "optical transducer" refers to the part of the sensor that detects and transforms the optical signal resulting from the interaction of the chemical and/or biological pathogen with the nanoprobe into another signal that can be more easily measured and quantified. In some embodiments, the optical transducer uses colorimetry or transmittance spectroscopy to detect the pathogen.

As used herein, a "photodetector" is a device used for the detection of light. Non-limiting examples of photodetectors include a microscope (e.g., a fluorescence microscope) and an optical spectrometer (e.g., a fiber optic spectrometer). In some embodiments, the photodetector comprises a microscope or a spectrometer. In some embodiments, the photodetector comprises a confocal fluorescence microscope or a fiber optic spectrometer.

Channel 212 of flow cell 210 of fluidic sensor system 200 may be filled with a sample liquid 224. As used herein, the terms "sample" and "liquid sample" refer to a liquid that can be tested for chemical or biological contamination using the presently disclosed sensor system. In some embodiments, the sample is originally found as a liquid, such as water or milk. In other embodiments, fluid is extracted out of a sample, such as a vegetable, fruit, and the like, to form a filtered food sample. In still other embodiments, a sample is mixed with a liquid and the liquid is tested. As used herein, the term "analyte" refers to a component found in a liquid, such as a chemical and/or biological pathogen found in a water sample.

Sample liquid 224 may or may not contain a target pathogen 226 and a non-target organism 228. As used herein, the term "pathogen" refers to a chemical or biological species, such as an ion, organic compound, bacteria, virus, or parasite capable of producing disease. In some embodiments, the presently disclosed subject matter discloses a sensor system and methods for detecting at least one chemical pathogen. As used herein, the term "chemical pathogen" refers to a chemical that can cause disease, such as ion pathogens, organic compounds, and the like. Non-limiting examples of ion pathogens include mercury, copper, lead, indium, titanium, chromium, cobalt, zinc, cadmium, manganese, arsenic, potassium, calcium, sulfate, chloride, ammonium, and thiocyanate. Non-limiting examples of organic compounds include generally organic compounds derived from detergents, disinfection byproducts, food processing waste, insecticides, herbicides, petroleum-based hydrocarbons, including gasoline, diesel fuel, jet fuels, fuel oil, motor oil, lubricants, and fuel combustion byproducts, volatile organic compounds, including industrial solvents, chlorinated solvents, and pharmaceutical drugs and their metabolites. Particular organic compounds include, but are not limited to, aldrin, chlordane, dieldrin, endrin, heptachlor, hexachlorobenzene, mirex, toxaphene, polychlorinated biphenyls, dichlorodiphenyltrichloroethane, dioxin, and polychlorinated dibenzofurans.

In some embodiments, the presently disclosed subject matter discloses a sensor system and methods for detecting at least one biological pathogen. As used herein, the terms "biological pathogen" and "microbial pathogen" refer to a biological agent that can cause disease, such as bacteria, viruses, protozoa, protists (e.g., algae), archaea, fungi (e.g., yeast and molds), parasites, and the like. As used herein, the terms "bacterium" and "bacteria" refer to one-celled organisms comprising the Schizomycota, a phylum of the kingdom Monera. It will be appreciated by one with ordinary skill in the art that there may be overlap between the biological agents that cause disease. For example, a biological agent may be both a parasite and a fungi.

Non-limiting examples of bacterial pathogens include *Bacillus, Brucella, Burkholderia, Francisella, Yersinia, Streptococcus, Haemophilus, Nisseria, Listeria, Clostridium, Klebsiella, Legionella, Escherichia* (e.g., *E. coli*), *Mycobacterium, Staphylococcus, Campylobacter, Vibrio,* and *Salmonella*, as well as drug and multidrug resistant strains and highly virulent strains of these pathogenic bacteria. Non-limiting examples of known food-borne bacterial pathogens include *Salmonella, Clostridium, Campylobacter* spp., *Staphylococcus, Salmonella, Escherichia* (e.g., *E. coli*), and *Listeria*. In some embodiments, non-limiting examples of bacterial pathogens include *Bacillus anthracis, Brucella abortus, Brucella melitensis, Brucella suis, Burkholderia mallei, Burkholderia pseudomallei, Francisella tularensis, Yersinia pestis, Streptococcus* Group A and B, MRSA, *Streptococcus pneumonia, Haemophilus influenza, Nisseria meningitides, Listeria monocytegenes, Clostridium difficile, Klebsiella,* highly virulent pathogenic strains of *E. coli, Mycobacterium tuberculosis, Staphylococcus aureus, Campylobacter* spp, *Salmonella* spp, and *Clostridium perfringens*, as well as drug and multidrug resistant strains and highly virulent strains of these pathogenic bacteria. In some embodiments, non-limiting examples of known food-borne bacterial pathogens include *Salmonella,* nontyphoidal *Clostridium perfringens, Campylobacter* spp., *Staphylococcus aureus, Salmonella*, nontyphoidal, *Campylobacter* spp., *E. coli* (STEC) 0157, and *Listeria monocytogenese.*

Non-limiting examples of viruses found in water and/or food include enterovirus, hepatovirus, reovirus, rotavirus, adenovirus, calicivirus (e.g., norovirus, sapovirus), astrovirus, parvovirus, coronavirus, and torovirus. Non-limiting examples of food-borne viruses include hepatitis A, norovirus (e.g., Norwalk virus), and rotavirus.

Non-limiting examples of parasites include *Trichinella, Anisakis, Schistosoma, Dracunculus, Taenia, Fasciolopsis, Echinococcus, Enterobius, Ascaris, Cryptosporidium* and *Cyclospora.* In some embodiments, non-limiting examples of parasites include *Cryptosporidium parvum* and *Cyclospora cayetanenesis.* Non-limiting examples of fungi include yeast and molds. Non-limiting examples of fungi include *Aspergillus, Cladosporium, Epicoccum, Penicillium, Acremonium, Exophiala, Phialophora, Trichoderma, Fusarium, Phoma, Mucorales, Geotrichum, Candida,* and *Claviceps.* Non-limiting examples of protists include *Trypanosoma* and *Plasmodium.* Non-limiting examples of protozoa include *Entamoeba, Cryptosporidium, Cyclospora, Giardia,* and *Microsporidia.*

In some embodiments, at least one biological pathogen is selected from the group consisting of a bacterium, protozoan, protist, fungus, parasite, and a virus. In some embodiments, at least one microbial pathogen is selected from the group consisting of a bacteria and a virus. In some embodiments, at least one pathogen is selected from the group consisting of a bacterium and a virus. In some embodiments, at least one microbial pathogen is *Escherichia coli* (*E. coli*) or norovirus. In some embodiments, at least one pathogen is *Escherichia coli* (*E. coli*) or a norovirus. In some embodiments, at least one chemical and/or biological pathogen is *Escherichia coli* (*E. coli*) or a norovirus.

Non-target organism 228 may be a non-targeted microorganism and/or other organism.

In operation, multifunctional nanoprobe 100 is added to sample liquid 224, wherein sample liquid 224 may or may not contain target pathogen 226 and non-target organism 228. Sample liquid 224 can be incubated for a period of time sufficient to form a nanoprobe/pathogen conjugate 230. Sample liquid 224 is flowed into channel 212 through input 214 and out of channel 212 through output 216. As sample liquid 224 is flowed through channel 212, nanoprobe/pathogen conjugate 230 is captured by magnet 218. Non-target organism 228 and unbound multifunctional nanoprobe 100 are not captured by magnet 218 and are flowed out of channel 212 through output 216. Light from LED 220 is used to stimulate plasmonic nanoparticle 110 of nanoprobe 100 in the captured nanoprobe/pathogen conjugate 230. The optical signal from plasmonic nanoparticle 110 is detected and transduced by photodetector 222 into another signal that is readily measured and quantified.

III. Methods for Multifunctional Nanoprobe-Enabled Capture and Early Detection of Pathogens The presently disclosed subject matter also provides methods for the capture and early detection of chemical or biological pathogens by using the presently disclosed sensor. The presently disclosed methods can be used quickly to detect in real-time or near real-time a pathogen, particularly a food- or water-borne pathogen, under field conditions. As used herein, the terms "real-time" and "near real-time" refer to the detection of a pathogen in a few minutes or less from when a sample is obtained. In some embodiments, determining the existence or absence of a pathogen occurs in real-time. In some embodiments, determining the presence of at least chemical and/or biological pathogen occurs in real-time.

In some embodiments, the presently disclosed subject matter provides a method for determining the presence of at least one chemical and/or biological pathogen in a liquid sample, the method comprising: (a) providing a sensor system comprising: (i) at least one nanoprobe comprising a plasmonic nanoparticle and a magnetic particle; (ii) a flow cell comprising a channel capable of holding a liquid sample comprising at least one chemical and/or biological pathogen and the at least one nanoprobe; (iii) a magnet placed in close proximity to the flow of the liquid sample, wherein the magnet is capable of capturing the at least one nanoprobe when the at least one nanoprobe is bound to the at least one chemical and/or biological pathogen; and (iv) an optical transducer comprising a light source and a photodetector, wherein the optical transducer is capable of detecting the at least one nanoprobe bound to the at least one chemical and/or biological pathogen; (b) contacting a liquid sample comprising at least one chemical and/or biological pathogen with the at least one nanoprobe comprising a plasmonic nanoparticle and a magnetic particle to form at least one nanoprobe conjugated with at least one chemical and/or biological pathogen; (c) adding the liquid sample comprising the at least one nanoprobe conjugated with at least one chemical and/or biological pathogen to the channel of the flow cell; (d) capturing the at least one nanoprobe conjugated with at least one chemical and/or biological pathogen using the magnet; and (e) detecting the presence of the at least one nanoprobe conjugated with at least one chemical and/or biological pathogen using the optical transducer, thereby detecting the presence of at least one chemical and/or biological pathogen in the liquid sample.

FIG. 3 shows a flow diagram of an example of a method 300 of using multifunctional nanoprobe 100 and fluidic sensor system 200 for determining the existence or absence of a pathogen in a sample. Method 300 includes, but is not limited to, the following steps.

At a step 310, a sample is obtained. For example, the sample is sample liquid 224 that may or may not contain targeted pathogen 226 and/or a non-targeted organism 228.

At a step 315, multifunctional nanoprobe 100 is added to sample liquid 224.

At a step 320, nanoprobe/pathogen conjugates 230 are formed. For example, sample liquid 224 with multifunctional nanoprobe 100 therein is incubated for a period of time sufficient to form nanoprobe/pathogen conjugates 230.

At a step 325, the sample mixture is loaded in the fluidic sensor. For example, sample liquid 224 with nanoprobe 100 therein is flowed into channel 212 through input 214 and out of channel 212 through output 216.

At a step 330, nanoprobe/pathogen conjugates 230 are captured. For example, as sample liquid 224 is flowed through channel 212, nanoprobe/pathogen conjugates 230 are captured by magnet 218. Non-target organism 228 and unbound multifunctional nanoprobe 100 are not captured by magnet 218 and are flowed out of channel 212 through output 216.

At a step 335, the presence or absence of captured nanoprobe/pathogen conjugates 230 is detected. For example, light from LED 220 is used to stimulate plasmonic nanoparticle 110 of nanoprobe 100 in the captured nanoprobe/pathogen conjugate 230. The optical signal from plasmonic nanoparticle 110 is detected and transduced by photodetector 222 into another signal that is readily measured and quantified.

In some embodiments, the presently disclosed method can detect at least one chemical and/or biological pathogen at a concentration of about 20, 15, 10, 9, 8, 7, 6, 5, 4, 3, 2, or 1 cfu/mL or less. In some embodiments, the presently disclosed method can detect at least one chemical and/or biological pathogen at a concentration of about 10 cfu/mL or less. In some embodiments, the presently disclosed method can detect a pathogen at a concentration of about 10 cfu/mL or less.

In some embodiments, adding the liquid sample comprising at least one nanoprobe conjugated with at least one chemical and/or biological pathogen to the channel of the sensor system occurs before or concurrently with contacting the liquid sample comprising at least one chemical and/or biological pathogen to at least one nanoprobe comprising a plasmonic nanoparticle and a magnetic particle to form at least one nanoprobe conjugated with at least one chemical and/or biological pathogen. In some embodiments, adding the sample to the channel of the sensor system disclosed herein occurs before or concurrently with allowing at least one nanoprobe to react with at least one pathogen if present in the sample to form at least one nanoprobe conjugated with a pathogen.

In some embodiments, the nanoprobe is functionalized with at least one targeting molecule via a linker molecule. In some embodiments, at least one targeting molecule is selected from the group consisting of an antibody, an enzyme, a peptide, a protein, a nucleic acid, and an oligonucleotide. In some embodiments, at least one targeting molecule is an antibody. In some embodiments, at least one targeting molecule is an immunoglobulin G (IgG) antibody.

In some embodiments, at least one biological pathogen is selected from the group consisting of a bacterium, protozoan, protist, fungus, parasite, and a virus. In some embodiments, at least one chemical and/or biological pathogen is *Escherichia coli* (*E. coli*) or a norovirus.

In some embodiments, the magnet is a solenoid. In some embodiments, the light source is a light emitting diode (LED). In some embodiments, the photodetector comprises a microscope or a spectrometer.

In some embodiments, the plasmonic nanoparticle comprises gold, silver, nickel, copper, titanium, silicon, galadium, palladium, platinum, and/or chromium. In some embodiments, the magnetic particle comprises iron, nickel, and/or cobalt.

In some embodiments, the linker molecule comprises a polyether linkage. In some embodiments, the linker molecule comprises a HS-polyethylene glycol-COOH linkage or a dopamine-polyethylene glycol-COOH linkage.

In some embodiments, the liquid sample comprises filtered food and/or water.

IV. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Nanoprobe Biofunctionalized with IgG Antibodies

In this Example, $E.$ $coli$ and norovirus specific immunoglobulin G (IgG) antibodies are anchored onto Au—$Fe_3O_4$ heterodimer nanoparticles to form a presently disclosed nanoprobe. Corresponding food-borne pathogens can be captured and detected using the nanoprobe (FIG. 1A and FIG. 1B). These nanoparticles will first be transferred from organic phase to aqueous solutions by ligand exchange, with hydrophilic polyethylene glycol (PEG, with HS-PEG-COOH for Au and dopamine-PEG-COOH for $Fe_3O_4$) molecules replacing oleylamine and/or oleic acid that were used as surfactant in the nanoparticle synthesis. The water-soluble nanoparticles will then be conjugated with IgG antibodies specific to the microorganism of interest through amide bonds. This nanoprobe comprising nanoparticles and antibodies will then be mixed with fluids extracted out of food samples (e.g., vegetables, milk) containing $E.$ $coli$ CN13 (a non-pathogenic laboratory strain of $E.$ $coli$) or murine norovirus (a non-pathogenic human norovirus surrogate), and flown through a glass channel equipped with a solenoid. The nanoparticle conjugated microorganisms will be captured by the magnetic field, the strength of which will be optimized to allow free magnetic nanoparticles to be carried away by the flow.

For optical detection, at least two methods can be used. The first one is imaging by a confocal fluorescence microscope, e.g., at an excitation wavelength of 561 nm and imaging wavelength with the range of 650-700 nm. It is noticed that individual norovirus might not be visualized due to their small size (<40 nm), but the captured viruses could be imaged as an aggregate. Alternatively, a fiber optic spectrometer operating at the UV/Vis wavelength region (360-880 nm) will be incorporated onto the glass channel. This embodiment will provide in-line detection of the optical signals from plasmonic Au in the nanoprobes, enabling real-time monitoring of the accumulation of captured microorganisms. The presently disclosed device and methods allow for the amount of captured pathogens to be proportional to the concentration, the flow rate and the time that the solenoid has been on. Therefore, early detection at ultralow concentrations can be achieved simply by extending the time of capturing.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A sensor system for detecting at least one chemical and/or biological pathogen in a liquid sample, the sensor system comprising: (a) a nanoprobe comprising a heterodimer nanoparticle comprising a plasmonic nanoparticle and a magnetic nanoparticle, wherein the plasmonic nanoparticle and magnetic nanoparticle comprise separate nanoparticles adjoined alongside one another; (b) a flow cell comprising a channel capable of holding a liquid sample comprising at least one chemical and/or biological pathogen and the nanoprobe; (c) a magnet placed in close proximity to the flow of the liquid sample, wherein the magnet is capable of capturing the nanoprobe when the nanoprobe is bound to the at least one chemical and/or biological pathogen; and (d) an optical transducer comprising a light source and a photodetector, wherein the optical transducer is capable of detecting the nanoprobe bound to the at least one chemical and/or biological pathogen, wherein the sensor system is capable of detecting the at least one chemical and/or biological pathogen in a liquid sample at a concentration of about 10 colony-forming units (cfu)/mL or lower in real time.

2. The sensor system of claim 1, wherein the nanoprobe is functionalized with at least one targeting molecule via a linker molecule.

3. The sensor system of claim 2, wherein the at least one targeting molecule is selected from the group consisting of an antibody, an enzyme, a peptide, a protein, a nucleic acid, and an oligonucleotide.

4. The sensor system of claim 3, wherein the at least one targeting molecule is an antibody.

5. The sensor system of claim 4, wherein the antibody is an immunoglobulin G (IgG) antibody.

6. The sensor system of claim 1, wherein the photodetector comprises a microscope or a spectrometer.

7. The sensor system of claim 1, wherein the magnet is optimized to capture the nanoprobe when it is bound to the at least one chemical and/or biological pathogen and not capture the nanoprobe when it is not bound to the at least one chemical and/or biological pathogen.

8. The sensor system of claim 1, wherein the magnet is a solenoid.

9. The sensor system of claim 1, wherein the light source is a light emitting diode (LED).

10. The sensor system of claim 1, wherein the plasmonic nanoparticle comprises gold, silver, nickel, copper, titanium, silicon, galadium, palladium, platinum, and/or chromium.

11. The sensor system of claim 1, wherein the magnetic nanoparticle comprises iron, nickel, and/or cobalt.

12. The sensor system of claim 2, wherein the linker molecule comprises a polyether linkage.

13. The sensor system of claim 12, wherein the linker molecule comprises a HS-polyethylene glycol-COOH linkage or a dopamine-polyethylene glycol-COOH linkage.

14. The sensor system of claim 1, wherein the at least one biological pathogen is selected from the group consisting of a bacterium, protozoan, protist, fungus, parasite, and a virus.

15. The sensor system of claim 14, wherein the at least one chemical and/or biological pathogen is *Escherichia coli* (*E. coli*) or a norovirus.

16. The sensor system of claim 1, wherein the liquid sample comprises filtered food and/or water.

\* \* \* \* \*